United States Patent
Shimamoto

(10) Patent No.: US 8,080,412 B2
(45) Date of Patent: Dec. 20, 2011

(54) MULTIWELL INCUBATION APPARATUS AND METHOD OF ANALYSIS USING THE SAME

(75) Inventor: Nobuo Shimamoto, Mishima (JP)

(73) Assignee: Research Organization of Information and Systems, Tokyo (JP)

( * ) Notice: Subject to any disclaimer, the term of this patent is extended or adjusted under 35 U.S.C. 154(b) by 465 days.

(21) Appl. No.: 12/297,011

(22) PCT Filed: Apr. 13, 2007

(86) PCT No.: PCT/JP2007/000409
§ 371 (c)(1),
(2), (4) Date: Oct. 13, 2008

(87) PCT Pub. No.: WO2007/122814
PCT Pub. Date: Nov. 1, 2007

(65) Prior Publication Data
US 2009/0170714 A1    Jul. 2, 2009

(30) Foreign Application Priority Data

Apr. 13, 2006    (JP) .................................. 2006-110713

(51) Int. Cl.
*C12M 1/00*    (2006.01)
*C12M 3/00*    (2006.01)
*F28F 3/12*    (2006.01)
(52) U.S. Cl. ............... 435/303.1; 435/305.1; 435/305.2; 435/294.1; 435/307.1; 506/7; 506/33; 506/43; 165/168; 165/169; 165/170
(58) Field of Classification Search ............... 435/303.1, 435/305.1, 305.2, 294.1, 307.1; 506/7, 33, 506/43; 165/168, 169, 170
See application file for complete search history.

(56) References Cited

U.S. PATENT DOCUMENTS

| | | | |
|---|---|---|---|
| 4,673,651 A | * | 6/1987 | Rothenberg et al. ....... 435/305.2 |
| 4,865,987 A | | 9/1989 | Seppo |

(Continued)

FOREIGN PATENT DOCUMENTS

| | | |
|---|---|---|
| EP | 0 290 722 | 11/1988 |
| EP | 0 290 722 A2 | 11/1988 |
| JP | 2003 289848 | 10/2003 |
| WO | 90 10689 | 9/1990 |
| WO | 02 30561 | 4/2002 |

*Primary Examiner* — Nathan Bowers
(74) *Attorney, Agent, or Firm* — Oblon, Spivak, McClelland, Maier, & Neustadt, L.L.P.

(57) ABSTRACT

A continuous temperature-gradient incubation apparatus designed to solve the problem of moving of liquid vapor generated on the high-temperature side toward the low-temperature side to thereby cause condensation.

There is provided a multiwell incubation apparatus having a well-housing vessel made of a heat conducting material and, detachably housed therein, liquid-storing wells, the wells being arranged in transverse rows and longitudinal rows, the multiwell incubation apparatus being also provided with a liquid or gas flow channel or bath for supply of a gas saturated with vapor of the liquid, the multiwell incubation apparatus being capable of maintaining incubation temperatures differing between individual transverse rows of wells with a predetermined temperature difference, so as to realize a temperature series which forms a predetermined temperature difference profile along the longitudinal rows, characterized in that the multiwell incubation apparatus includes a heat source for realizing a temperature which is the lowest in the given temperature series, the heat source being disposed outside the well rows and along the transversely lined up wells close to a first side of the housing vessel; another heat source for realizing a temperature which is the highest in the given temperature series, the heat source being disposed outside the well rows and along a side opposite to the first side; and a separator provided for each transverse row of a certain temperature.

15 Claims, 11 Drawing Sheets

U.S. PATENT DOCUMENTS

| | | |
|---|---|---|
| 5,240,857 A | 8/1993 | Laehetkangas |
| 6,673,595 B2 * | 1/2004 | Barbera-Guillem ....... 435/286.2 |
| 6,716,629 B2 | 4/2004 | Hess et al. |
| 7,867,752 B1 * | 1/2011 | Greenberger et al. ..... 435/286.1 |
| 2002/0094533 A1 | 7/2002 | Hess et al. |
| 2003/0124716 A1 | 7/2003 | Hess et al. |
| 2003/0180807 A1 | 9/2003 | Hess et al. |
| 2008/0032397 A1 * | 2/2008 | Korpinen ................... 435/303.1 |

* cited by examiner

MULTIWELL INCUBATION APPARATUS AND METHOD OF ANALYSIS USING THE SAME

FIELD OF THE INVENTION

The present invention relates to a multiwell incubation apparatus which provides, in a single apparatus, a plurality of different incubation temperatures within a predetermined temperature range, and to a method of analysis using such an apparatus.

BACKGROUND OF THE INVENTION

Analyses using microbial cells or other biological specimens have been performed, for example, by inoculating microbes on an agar medium and observing them by the naked eye after they are maintained for a certain period of time at a constant temperature in an incubator. In recent years, however, liquid culture has become more popular, which employs a multiwell plate having a plurality of wells. Moreover, for chemical reactions involved in, for example, combinatorial chemistry, multiwell plates are often used to perform analysis of many specimens.

Usually, the above-mentioned liquid culture and specimen analyses are performed as follows: Specimens are added to the wells of a multiwell plate and cultured while maintained at a predetermined temperature for a predetermined period of time, followed by irradiation with light. Subsequently, transmitted light or scattering light including fluorescence is measured.

Hitherto, for maintaining a temperature of a multiwell plate, the plate is typically placed on a flat heat-retentive plate. Also, in practice of retaining temperature of a multiwell plate, an incubation apparatus having shelves provided with such heat-retentive plates is employed (see Patent Document 1).

However, when incubation is performed under a variety of different temperature conditions, intricate manipulation is required. That is, an incubation apparatus must be provided for each temperature, and multiwell plates must be placed in a plurality of incubation apparatuses, each of which has been set at a specific temperature.

Moreover, for performing analyses, the multiwell plates must be taken out of the incubation apparatuses, which is also inconvenient.

In order to solve these problems, there has been proposed a so-called continuous temperature-gradient incubation apparatus, which employs a heat-conductive container having a plurality of orderly arranged wells, wherein one end of the container is set at a high temperature and the other end is set at a low temperature (see Patent Documents 2 to 4).

[Patent Document 1] JP-A 2003-289848
[Patent Document 2] WO90/10689
[Patent Document 3] EP-A 0290722
[Patent Document 4] U.S. Pat. No. 4,865,987

DISCLOSURE OF THE INVENTION

Problems to be Solved by the Invention

Such continuous temperature-gradient incubation apparatuses, however, have encountered a new problem caused by gas exchange occurring in the temperature gradient. That is, vapor generated from the liquid on the high-temperature side moves to the low-temperature side and condenses. More specifically, condensation occurring on the low-temperature side produces water droplets within the wells, leading to not only dilution of the test specimen to change the culture conditions but also overflow of the liquid. Thus, those temperature-gradient incubation apparatuses could not be applied to practical use.

Therefore, an object of the present invention is to provide a simultaneous multi-temperature incubation apparatus which, in a single apparatus, allows a plurality of temperature settings and requires no work for transferring the wells, wherein the problems caused by travel of liquid vapor and condensation into liquid are solved by regulation of the vapor pressure.

Means to Solve the Problems

The present inventors have conducted extensive studies, and have found that all the above problems can be solved by the following design. That is, a plurality of wells are arranged in rows and housed in a heat-conductive-material made container, one end of which is set at a high temperature and the other end is set at a low temperature; well rows are separated in terms of temperature so as to prevent gas communication therebetween; and each row of wells is provided with a liquid or gas flow channel or bath for regulating vapor pressure, to thereby achieve a uniform temperature prevailing within each row of wells and to allow positive compensation to be effected against any change in liquid volume which would otherwise be caused by the transfer of liquid vapor. In this configuration, the continuous temperature gradient is replaced by a plurality of temperatures with predetermined temperature differences, and a measurement is performed for those temperatures simultaneously. Moreover, the inventors have found that, if light emitted through observation light paths provided for each row is scanned two-dimensionally, extra work for removing the wells before analysis is no longer required, to thereby achieve the present invention.

Accordingly, the present invention provides a multiwell incubation apparatus having a well-housing vessel made of a heat conducting material and, detachably housed therein, wells for storing liquid, the wells being arranged in transverse rows and longitudinal rows, the multiwell incubation apparatus being also provided with a liquid or gas flow channel or bath for supply of a gas saturated with vapor of the liquid, the multiwell incubation apparatus being capable of maintaining incubation temperatures differing between individual transverse rows of wells with a predetermined temperature difference, so that the temperatures realize a temperature series which forms a predetermined temperature difference profile along the longitudinal rows, characterized in that the multiwell incubation apparatus includes a heat source for realizing the lowest temperature of the given temperature series, the heat source being disposed outside the well rows and along the transversely lined up wells close to a first side of the housing vessel; another heat source for realizing a temperature which is the highest in the given temperature series, the heat source being disposed outside the well rows and along a side opposite to the first side; and a separator provided for each transverse row of a certain temperature.

The present invention also provides the multiwell incubation apparatus as described above, which further includes, in addition to the liquid or gas flow channel or bath for supply of a gas saturated with vapor of the liquid, separators disposed within a transverse row of a certain uniform temperature, so that changes in oxygen partial pressure or in partial pressure of a specific gas are realized in a staircase-like pattern within that row.

Moreover, the present invention provides an incubation method performed through use of the multiwell incubation apparatus as described above, which method comprises: adding specimens to the wells of the apparatus; and achieving, by use of the heat source along the first side of the well-housing vessel, a temperature which is the lowest within a predetermined temperature series, and also achieving, by use of the other heat source along the side opposite to the first side, a temperature which is the highest within the predetermined temperature series, to thereby realize incubation temperatures differing between individual transverse rows of wells, with a predetermined temperature difference.

Furthermore, the present invention provides a method of analysis of specimens, performed through use of the multiwell incubation apparatus as described above, characterized by: performing incubation of specimens through adding specimens to the wells of the apparatus, achieving, by use of the heat source along the first side of the well-housing vessel, a temperature which is the lowest within a predetermined temperature series, and also achieving, by use of the other heat source along the side opposite to the first side, a temperature which is the highest within the predetermined temperature series, to thereby realize incubation temperatures differing between individual transverse rows of wells, with a predetermined temperature difference; and irradiating the specimens contained in the wells with light, and measuring light transmitted through the specimens or scattered light including fluorescence.

EFFECTS OF THE INVENTION

With the incubation apparatus according to the present invention, a temperature series of equal intervals can be provided between the highest temperature and a temperature which is the lowest in a predetermined temperature range. Therefore, in a single run of incubation, several hundreds of experiments can be performed. Moreover, the user does not need to move the incubation apparatus before carrying out an analysis. In addition, since the problem of water evaporation from wells on the high temperature side and condensation on the low temperature side is eliminated, temperature-gradient culturing can be continued for a prolonged period of time, with small volumes of specimens. Therefore, the apparatus size can be reduced, and in addition, stacking of a number of such apparatus one on another enables the user to analyze the specimens under thousands of different conditions simultaneously. Furthermore, since the liquid or gas flow channel or bath is provided for each well row with an aim to regulate vapor pressure, a uniform temperature can be realized within a transverse row. When argon gas or nitrogen gas is allowed to flow through the flow channel, oxygen partial pressure in a well can be regulated, and likewise, partial pressure of a specific gas can be easily modified so as to provide a plurality of partial pressure conditions.

Therefore, the incubation apparatus according to the present invention enables culturing of microbes under different temperature conditions, which has previously been difficult, enables the user to find optimal culture temperatures, and realizes proliferation of microorganisms whose temperature conditions are unknown.

Figure 1:
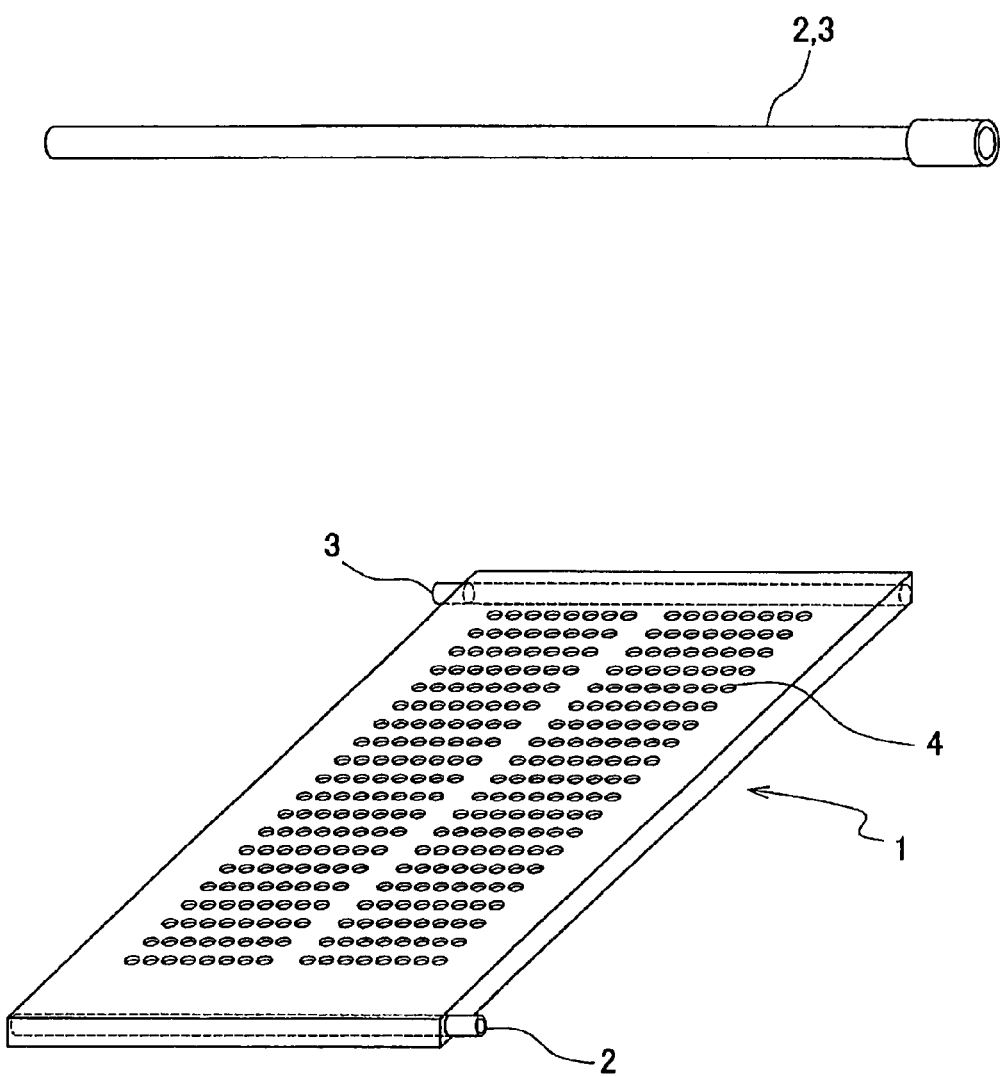
[FIG. 1] A perspective view of an exemplary incubation apparatus according to the present invention.

DESCRIPTION OF REFERENCE NUMERALS 1 multiwell incubation apparatus
2 flow channel
3 flow channel
4 well
5 observation hole
6 punched-out opening, or recess
7 observation hole
8 screw hole
9 sponge
11 upper tray (lid)
12 middle tray
13 lower tray
14 gasket
15 LED
16 bridge portion
17 heat pipe
18 solid heat source on the low-temperature side
19 solid heat source on the high-temperature side
20 hinge
21 motor
22 decelerator
23 cam
24 lever
25 liquid for maintaining saturated vapor pressure
26 flow channel for liquid or gas which is provided for maintaining saturated vapor pressure
27 reservoir for storing liquid for maintaining saturated vapor pressure
28 separator
29 flow channel provided for gas 1
30 flow channel provided for gas 2

DETAILED DESCRIPTION OF THE INVENTION

The present invention provides a multiwell incubation apparatus having a well-housing vessel made of a heat conducting material and, detachably housed therein, wells for storing liquid, the wells being arranged in transverse rows and longitudinal rows, the multiwell incubation apparatus being also provided with a liquid or gas flow channel or bath for supply of a gas saturated with vapor of the liquid, the channel or bath being disposed along a transverse row having a certain temperature, the multiwell incubation apparatus being capable of maintaining incubation temperatures differing between individual transverse rows of wells with a predetermined temperature difference, so that the temperatures realize a temperature series which forms a predetermined temperature difference profile along the longitudinal rows, characterized in that the multiwell incubation apparatus includes a heat source for realizing a temperature which is the lowest in the given temperature series, the heat source being disposed outside the well rows and along the transversely lined up wells close to a first side of the housing vessel; another heat source for realizing a temperature which is the highest in the given temperature series, the heat source being disposed outside the well rows and along a side opposite to the first side; and a separator provided for each transverse row of a certain uniform temperature.

Figure 3:
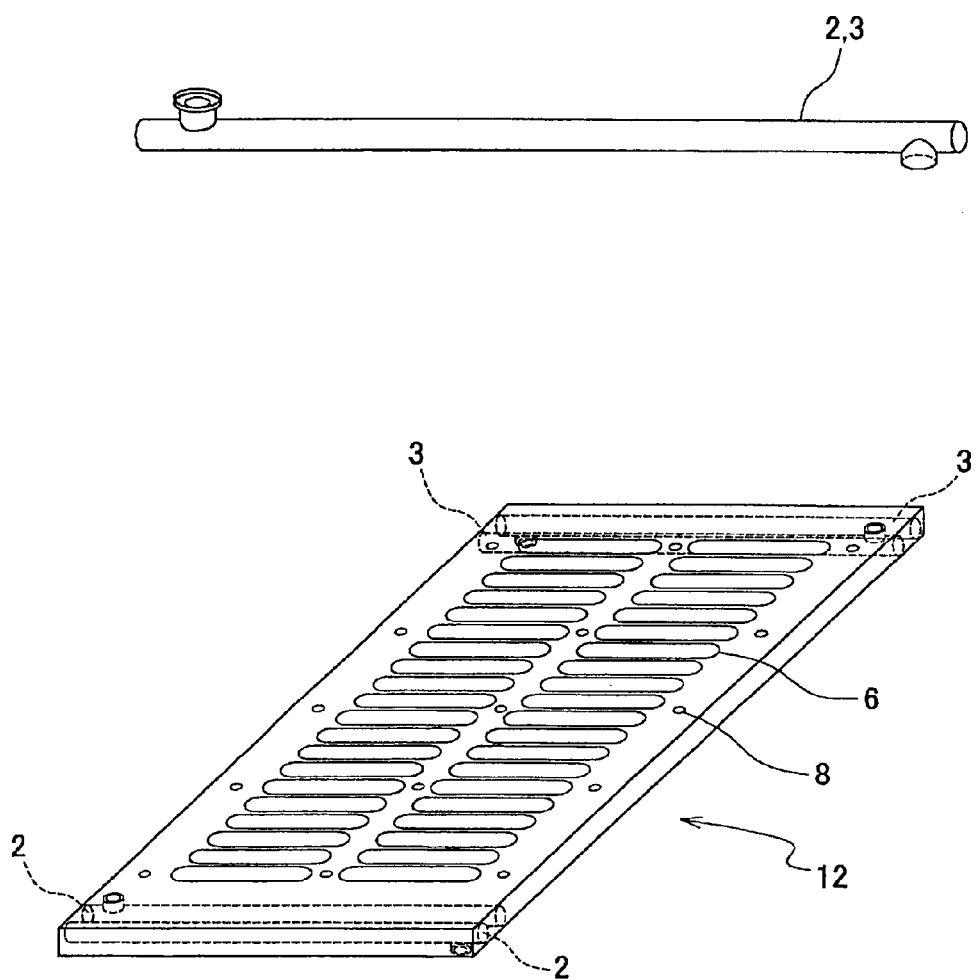
[FIG. 3] A perspective view showing another portion of the incubation apparatus.
Figure 4:
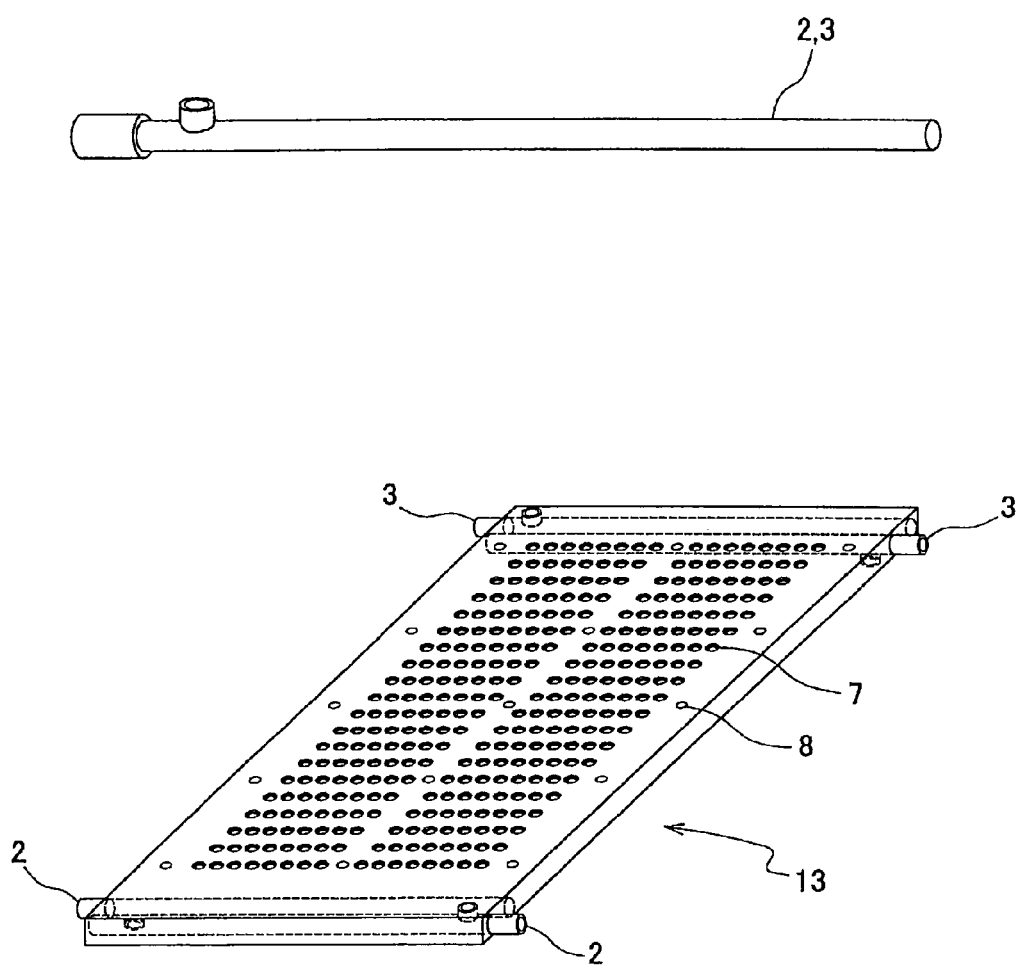
[FIG. 4] A perspective view showing yet another portion of the incubation apparatus.

The well-housing vessel of the incubation apparatus of the present invention should be made of heat conducting material in order to realize a plurality of different incubation temperatures. Among a variety of heat conducting materials, metal is preferred because it allows a broad range of processing. Specifically, aluminum, stainless steel, brass, copper, and the like are preferred, wherein aluminum and stainless steel are more preferred. In the housing vessel, wells which are arranged in transverse rows and longitudinal rows are detachably housed. To this end, recesses are provided for receiving the wells. Although one recess may be provided for one well, multi-well-accommodating recesses, each of which accommodates a well unit in which several wells are aligned and connected to each other, are preferred for attaining a uniform incubation temperature for each transverse row. That is, in a preferred embodiment of the housing vessel, as shown in FIGS. 3 and 4 in which water of different but constant temperatures are circulated as heat sources, there are provided a plurality of rows of recesses, each configured to receive a well unit in which several wells are aligned and connected to each other. With this configuration, in the longitudinal direction of well arrays; i.e., in the direction of flow channel 2 to flow channel 3 of water of constant temperature, the heat conducting material has a profile of recurrent pattern. As a result, this facilitates provision of an incubation temperature series in the longitudinal direction of the heat conducting material.

Also, in order to ensure heat conductivity, the socket of the well receiving portion preferably has such a depth that attains complete containment of a well excepting the upper portion thereof. Preferably, for preventing condensation, the temperature of the upper portion of the well is equal to or higher than the temperature of the well receiving portion. However, in the case of a higher temperature, the well is preferably made of a heat insulating material so that the temperature of the well is not affected.

No particular limitation is imposed on the number of the wells, arranged in transverse rows and longitudinal rows, in the incubation apparatus of the present invention, and the number can be determined as desired according to needs. For example, a transverse×longitudinal well array of 8×12, 8×20, 16×20, or 18×24 may be feasible. Preferably, wells are detachably housed in recesses of the mentioned housing vessel, with several transverse wells being connected to form a single body, as in FIGS. 3 and 4. Preferably, the wells are detachable individually or by well unit composed of several wells. Also, the wells are preferably made of a transparent plastic material, glass, or a similar material in order to obtain light paths required for performing photometric observation.

The incubation apparatus of the present invention has include, outside the well rows and along the transversely lined up wells close to a first side of the housing vessel, a heating device for attaining a temperature which is the lowest in the aforementioned predetermined temperature range or a flow channel allowing to pass a fluid of the lowest temperature therethrough; and also include, outside the well rows and along a side opposite to the first side, a heating device for attaining a temperature which is the highest in the mentioned predetermined temperature range or another flow channel allowing to pass a fluid of the highest temperature therethrough. For example, as shown in FIG. 4, when a fluid of low temperature is caused to flow through a flow channel 2 and a fluid of high temperature is caused to flow through a flow channel 3, the transverse rows of wells, which are present between the flow channel 2 and the flow channel 3, attain a series of incubation temperatures among them between the lowest and the highest temperatures. Here, the fluid may be gas or liquid, with liquid being preferred and water (or hot water) being more preferred.

Figure 10:
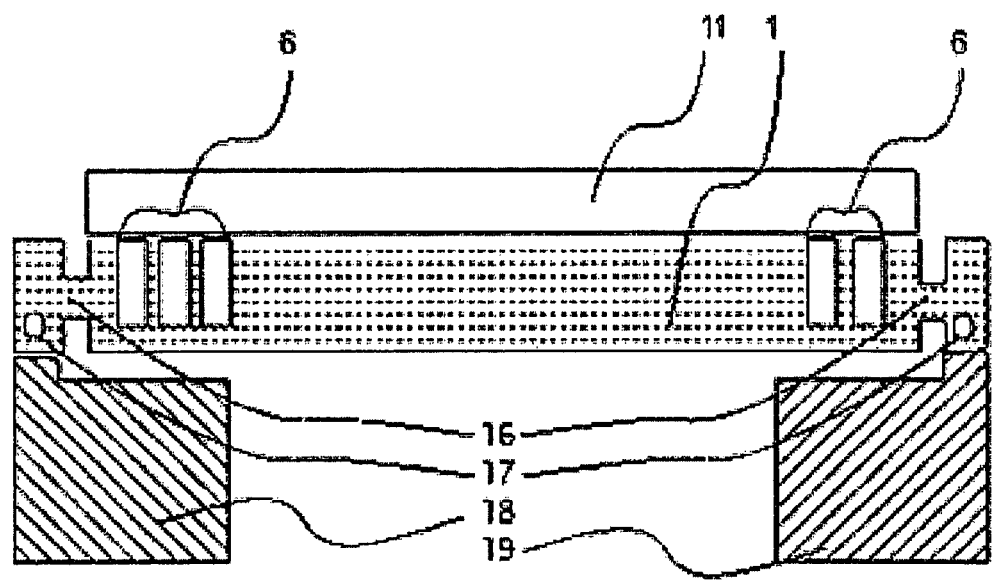
[FIG. 10] A cross section view of an exemplary incubation apparatus according to the present invention.

Alternatively, instead of including flow channels for passing the fluid therethrough, the main body (1) may be equipped with solid heating devices 18, 19 as shown in FIG. 10. Examples of the solid heating device include a heater and a Peltier element. When a solid heating device is employed, in order to reduce unevenness in temperature along either side of the housing vessel, a bridge portion, like the one shown in FIG. 10 by reference numeral 16, is preferably placed between each heat source and a corresponding recess wall of the housing vessel. Alternatively, provision of heat pipes 17 is also preferred. FIG. 10 shows such an example of housing vessel (1) having a lid (11) attached thereto.

The incubation apparatus of the present invention further includes a liquid or gas flow channel or bath along a transverse row of a certain uniform temperature for regulating the vapor pressure or the oxygen partial pressure above the wells belonging to the transverse row, and also includes a separator for every row of a certain uniform temperature, whereby the saturated vapor pressure of the liquid at that temperature can be maintained. With this structure, vapor is prevented from moving to other wells in the longitudinal direction, to thereby solve the problem that water evaporated from specimens on the high-temperature side condenses to form dew on the low-temperature side. The mentioned bath may be a porous material which has been impregnated with liquid.

Moreover, when a separator capable of delaying diffusion of gas is provided within a row of uniform temperature, oxygen partial pressure can be regulated by exposing one end of the well row which is a regulation target of oxygen partial pressure and supplying argon gas or nitrogen gas through a flow channel on the other side. This allows a user to find optimal oxygen partial pressure conditions in culturing an unknown microbe. In addition, since there can be realized culture conditions in which oxygen partial pressure differs for each longitudinal row, culturing can be performed under different conditions in terms of temperature and oxygen partial pressure simultaneously. Furthermore, when oxygen is replaced by other species of gas, an atmosphere which brings about a different chemical reaction can be realized within a row of uniform temperature.

Also, the incubation apparatus preferably has a lid thereon so that all the wells are covered thereby. The lid is useful for maintaining stable temperatures, preventing evaporation of liquid in wells and contamination with saprophytic bacteria, or for regulating vapor pressure or oxygen partial pressure.

Moreover, like the case of the main body of housing vessel, when the lid is equipped with a heat source along a first side thereof for realizing a temperature which is the lowest in a given temperature series and another heat source for realizing a temperature which is the highest in the given temperature series, the heat source being disposed outside the well rows and along a side opposite to the first side, temperature can be stabilized even more reliably.

Also, a middle tray may be provided between the housing vessel and the lid, and the middle tray may also be equipped with a heat source along a first side thereof for realizing a temperature which is the lowest in a given temperature series and another heat source for realizing a temperature which is the highest in the given temperature series, the heat source being disposed outside the well rows and along a side opposite to the first side.

When a housing vessel, a lid, and an optional middle tray are stacked one on another to thereby define recesses for receiving wells such that wells of a certain uniform temperature are accommodated within specific recesses, temperature stabilization of specimens is even more improved. Here, the middle tray may be formed as one section of the housing vessel.

When the lid and the housing vessel are both provided with holes at positions corresponding to the wells, each hole having a diameter smaller than that of the wells, the specimens can be visually observed. Also, through irradiation with light, any changes in absorbance, and scattering light including fluorescence can be measured. Alternatively, similar photometric observation is possible by providing, either above or below the respective wells, well observation holes which have a diameter smaller than that of the wells and a mirror for reflecting light for enabling optical observation or a light source.

Moreover, if a UV irradiation device is additionally provided such that, upon opening of the lid, UV rays are applied to the lid and also to the recesses of the housing vessel where wells are accommodated, germ sterilization can be performed before and after incubation.

Figure 11:
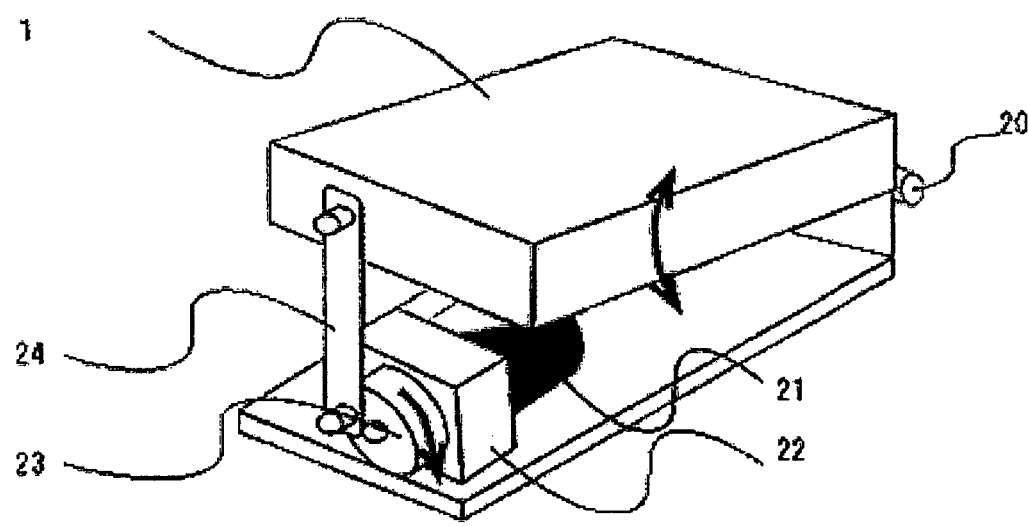
[FIG. 11] A perspective view of an exemplary shaker of an incubation apparatus according to the present invention.

The apparatus of the present invention may further include a shaker. The shaker may, for example, periodically tilt, by means of a lever 24, the entire body of a housing vessel and a middle tray to which a lid has been attached, or a stack 1 of a number of such entire bodies, the lever being linked with a cam 23 rotated through a decelerator 22 driven by a motor 21 (FIG. 11).

In one exemplary method according to the present invention, the apparatus of the present invention is employed, and incubation is performed under creation of a predetermined temperature series in which different incubation temperatures, in a staircase pattern, are realized so that one temperature is assigned to one transverse row of wells.

With this method, as described above, an incubation temperature gradient having a predetermined temperature series can be obtained, allowing compensation of liquid vapor pressure, to thereby enable handling of solutions or suspensions having a volume of less than some hundreds of microliters. As a result, an incubation of more than hundreds of different conditions, including temperature conditions, can be implemented in a single run of experiment.

With the incubation apparatus of the present invention, specimens can be analyzed by irradiating, during or after incubation, those specimens contained in the wells with light, and measuring light transmitted through the specimens or scattered light including fluorescence.

No particular limitation is imposed on the measuring method of light. For example, light is introduced through holes made in a lid of a housing vessel, and well-transmitted light is measured through holes provided below the housing vessel. Here, the light angle may be regulated by means of a Fresnel lens, and transmitted light may be measured by use of a commercially available scanner for a personal computer.

Alternatively, a movable apparatus equipped with a plurality of a photodetector may be employed, and transmitted light or scattered light including florescence emitted from a single row of observation holes is measured at a time, followed by measurement of light intensity in a scanning mode, in which respective rows are sequentially observed one by one in such a manner that wells belonging to one row are observed at a time.

These steps may be entirely or partially automated.

Photometric data obtained as described above may be automatically forwarded to a computer, with which automated numerical analyses suitable for cell-related experiments or chemical experiments designed on the basis of multiwell incubation may be performed, and values of target parameters may be automatically calculated and analyzed.

Moreover, the above measurement method can be automated by use of a computer, and also can be measured over a period of time. The obtained data can further be processed with a computer and can be recorded and stored as useful information.

Furthermore, if two or more of the above-described multiwell incubation apparatus are stacked one on another and data obtained from such multiwell incubation apparatuses are processed, it is possible to increase, by a factor of the number of the multiwell incubation apparatus, the number of different conditions under which examination is performed simultaneously.

The present invention will next be described in more detail with reference to the drawings.

An exemplary housing vessel which may be employed in the present invention is shown in FIG. 1.

The vessel 1 is provided with recesses for receiving a plurality of wells 4, and the wells 4 are accommodated therein.

A flow channel 2, through which a fluid of low temperature is passed, is provided along a first side of the vessel 1, and a flow channel 3, through which a fluid of high temperature is passed, is provided along a side opposite to the first side. When incubation is performed while allowing fluids of predetermined temperatures to pass through flow channels 2 and 3, the temperature of wells positioned close to the flow channel 3 approaches to the temperature of the high-temperature liquid, whereas the temperature of wells positioned close to the flow channel 2 approaches to the temperature of the low-temperature liquid, whereby the temperatures of the wells decrease stepwise from wells close to the flow channel 3 to those close to the flow channel 2, thereby achieving a temperature series of interest.

Therefore, a staircase-like series of incubation temperatures can be attained in a single vessel.

Thus, by housing wells in the housing vessel 1, performing incubation, irradiating the specimens in the wells with light, and measuring transmitted light or scattered light including fluorescence, changes occurring in specimens at respective temperatures can be analyzed easily.

Figure 12:
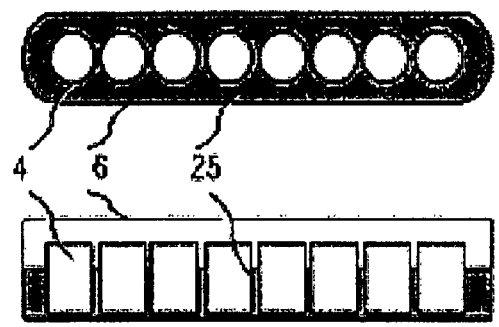
[FIG. 12] A diagram showing an exemplary flow channel or bath of an incubation apparatus according to the present invention.
Figure 13:
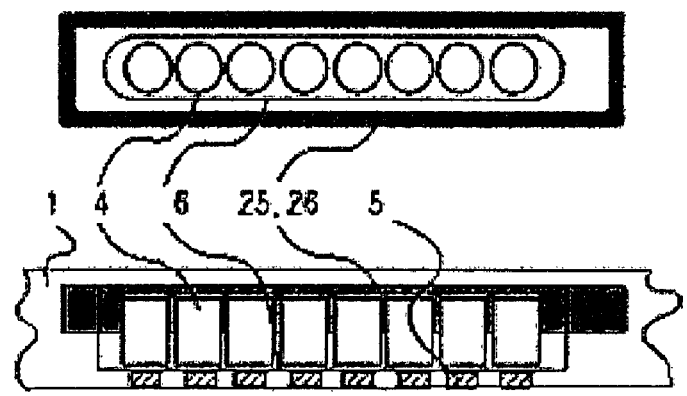
[FIG. 13] A diagram showing another exemplary flow channel or bath of an incubation apparatus according to the present invention.
Figure 14:
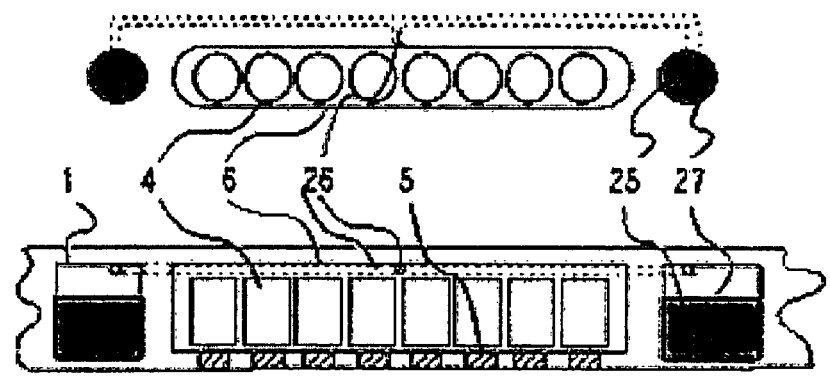
[FIG. 14] A diagram showing yet another exemplary flow channel or bath of an incubation apparatus according to the present invention.

Also, the apparatus of the present invention may be equipped with, along a transverse row of a certain uniform temperature, a liquid or gas flow channel or bath for maintaining vapor pressure of the liquid contained in the wells belonging to the transverse row at a saturated vapor pressure, and may also be equipped with separators within a transverse row of a certain uniform temperature. FIG. 12 shows one mode in which a liquid 25 for maintaining a saturated vapor pressure is directly added to a well-accommodating recess 6, or a variation mode in which a porous material impregnated with a liquid 25 for maintaining a saturated vapor pressure is added to a well-accommodating recess 6. FIG. 13 shows another mode in which a flow channel 26 surrounds the well-accommodating recess 6, so as to allow passage of the liquid 25 for maintaining a saturated vapor pressure therethrough. FIG. 14 shows yet another mode in which reservoirs 27 dedicated for a liquid 25 for maintaining a saturated vapor pressure is provided, so that only vapor of the liquid is introduced to a well-accommodating recess 6 via a dedicated flow channel 26.

FIGS. 2 to 7 respectively show preferred embodiments in relation to the incubation apparatus of the present invention.

Figure 2:
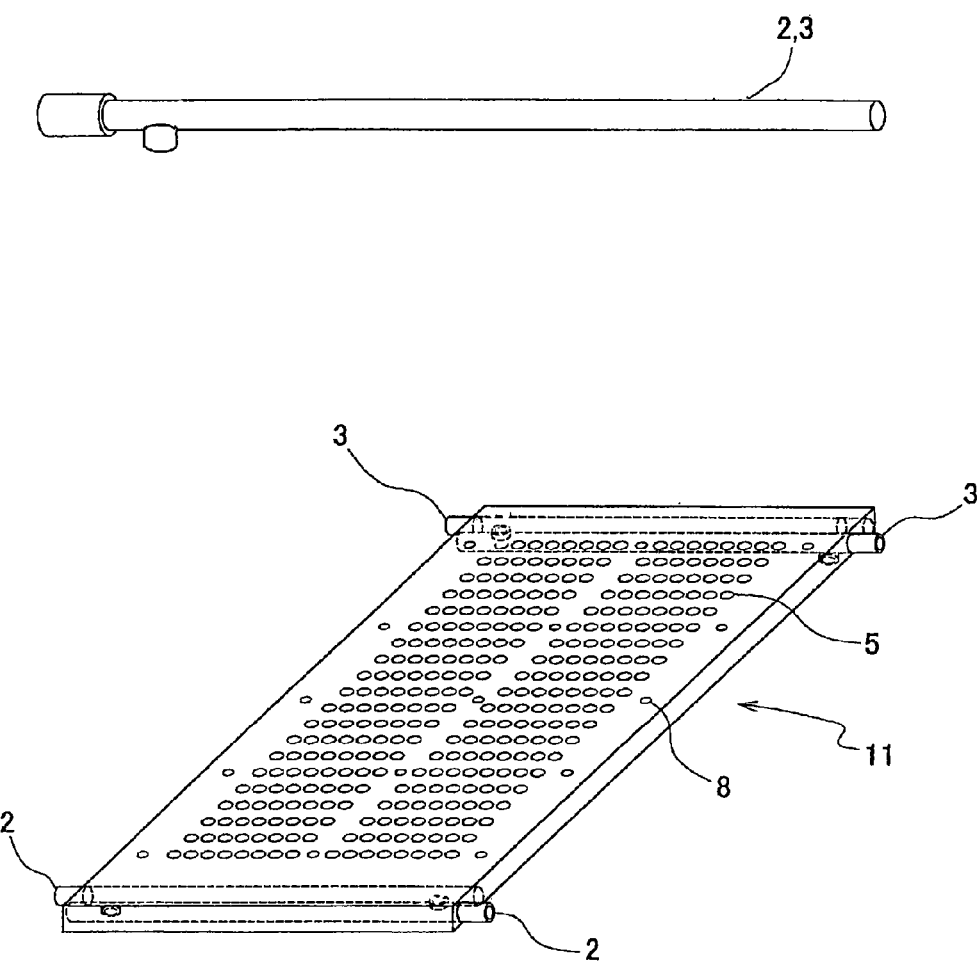
[FIG. 2] A perspective view showing a portion of an incubation apparatus which is an embodiment of the present invention.
Figure 7:
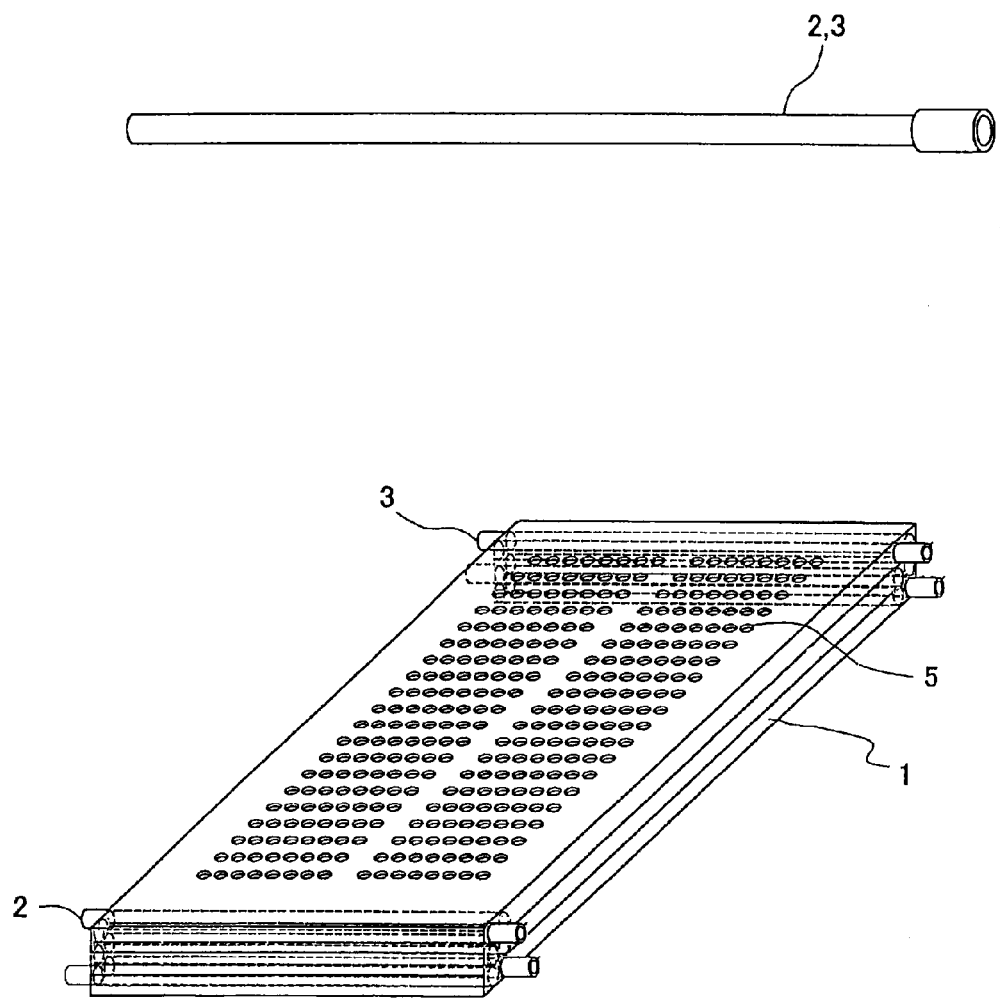
[FIG. 7] A perspective view of the incubation apparatus.

FIG. 2 shows a lid (upper tray) 11, FIG. 3 shows a middle tray 12, and FIG. 4 shows a lower tray 13. When the lid (upper tray) 11, the middle tray 12, and the lower tray 13 are laid one on another in this order from above, a united body of the three serves as an incubation apparatus (FIG. 7).

As will be seen in the middle tray, the punched-out opening serves as the recess 6 (FIG. 6) for receiving a well unit 4 having 8 wells (hereinafter may be referred to as an 8-well unit, see FIG. 5), whereby stable temperature conditions can be ensured.

Moreover, flow channels 2 and 3 penetrate each of the three trays, preventing occurrence of uneven temperatures between the upper and lower parts.

In addition, the lid 11 and the lower tray 13 are respectively provided with observation holes 5 and 7 at positions corresponding to the wells, allowing passage of light for analysis. Therefore, these holes enable the user to perform absorbance analysis or other analyses, not only after culturing of specimens, but also during the course of culturing.

Figure 15:
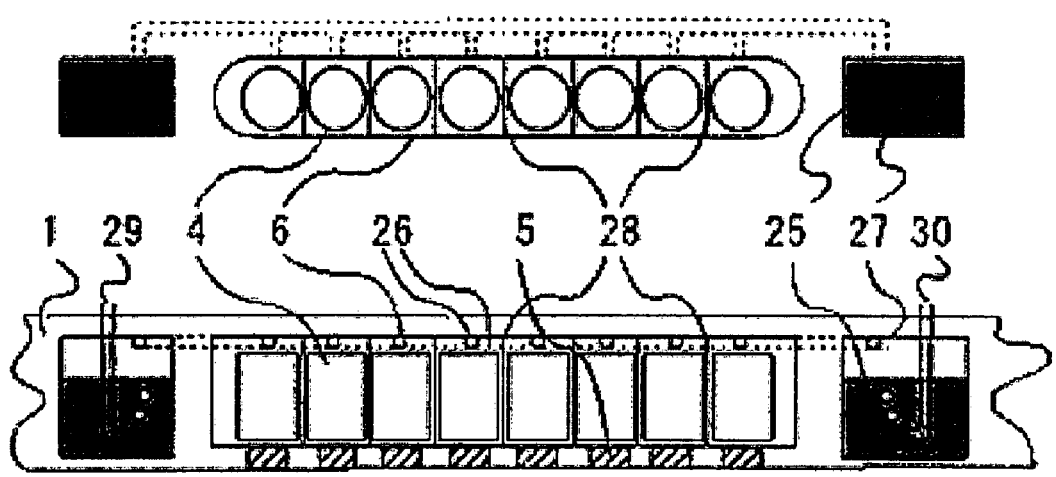
[FIG. 15] A diagram showing yet another exemplary flow channel or bath of an incubation apparatus according to the present invention.

FIG. 15 shows a configuration for attaining, in addition to attaining varied temperatures, a varying atmosphere (e.g., aerobic-anaerobic) of gas phase, among transverse rows of wells, while each of the transverse rows is maintained at a uniform temperature. The wells are individually independent so as to prevent gas phase communication therebetween, as they are separated by separator 28. To the reservoirs on either side, gases which are mutually different in species; e.g., air and nitrogen gas, are introduced such that a first gas is introduced to one reservoir and the second gas to the other reservoir, whereby the gases are saturated with the liquid in the reservoirs. The gases diffuse via a flow channel 26, and since the mixing ratio of the two gases varies with the distance from either reservoir, the gases supplied to the wells differ from well to well in terms of mixing ratio of gas components.

EXAMPLES

The present invention will next be described in detail with reference to Examples, etc., which should in no way be construed as limiting the invention thereto.

Example 1

As an incubation apparatus of the present invention, a housing vessel 1 as shown in FIG. 1 was produced. The outer dimensions of the vessel 1, made of aluminum plates, are 347 mm×222 mm×20 mm.

Each well socket 4 has a diameter of 6 mm and a depth of 13 mm.

As shown in FIG. 1, a flow channel 2 in the form of a single pipe is provided so as to run along and penetrate through one side of the apparatus. The pipe is made of aluminum and has an inner diameter of 8 mm. The flow channel 2 is connected to a tube extending from a thermostatic bath and also to another tube going back to the thermostatic bath, whereby water of a constant temperature can be circulated. The same situation applies to a flow channel 3.

With this configuration, the temperature of the incubation apparatus gradually changes from the highest temperature at the vicinity of the flow channel 3 to the lowest temperature at the vicinity of the flow channel 2, thereby attaining a plurality of incubation temperatures of a staircase profile.

Moreover, the present apparatus is provided with a liquid or gas flow channel or bath, along each row running in a transverse direction in which a certain uniform temperature prevails, for maintaining the vapor pressure of the liquid contained in the wells belonging to that row at a saturated vapor pressure. Also, separators are provided in each row of a certain specific temperature. Specifically, as shown in FIG. 12, a liquid 25 for maintaining a saturated vapor pressure is directly added to the interior of a well-accommodating recess 6.

Example 2

Similar to Example 1, another incubation apparatus was produced, wherein, instead of the section shown in FIG. 12 of the incubation apparatus of Example 1, a section shown in FIG. 13 was employed.

Example 3

Similar to Example 1, yet another incubation apparatus was produced, wherein, instead of the section shown in FIG. 12 of the incubation apparatus of Example 1, a section shown in FIG. 14 was employed.

Example 4

Similar to Example 1, yet another incubation apparatus was produced, wherein, instead of the section shown in FIG. 12 of the incubation apparatus of Example 1, a section shown in FIG. 15 was employed.

Example 5

Apparatuses of FIGS. 2 to 7, which are to be assembled into the incubation apparatus of the present invention, were fabricated. The dimensions of an upper tray 11, a middle tray 12, and a lower tray 13 are commonly 347 mm×222 mm×14 mm, and these trays are made of aluminum plates. The trays were placed one on another in this order, to thereby produce the incubation apparatus according to the present invention (FIG. 7), wherein at connecting portions of each tray at which two trays are connected to each other, gaskets 14 are provided. Also, screws were inserted into 14 screw holes provided for each tray, and the three trays were screw-fastened to each other to provide the united apparatus. Here, the center hole serves as an aperture through which reference light passes, wherein the reference light is used for correcting the light intensity of the light source provided for observation.

Figure 5:
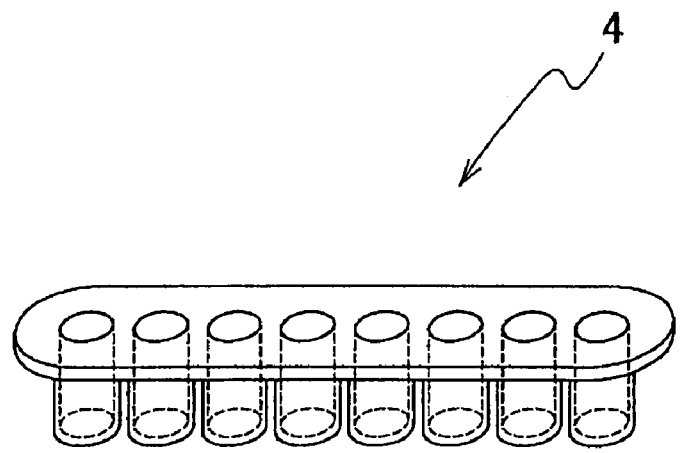
[FIG. 5] A perspective view showing a well-bearing portion to be incorporated into the incubation apparatus.

FIG. 5 shows a well unit 4, which in this case is an 8-well unit and is detachable from a housing vessel. The 8-well unit has a width of 12 mm and a length of 76 mm, and each well has an inner diameter of 6 mm and a depth of about 13 mm.

The well unit 4 is placed in a recess defined by a punched-out opening 6 of the middle tray 12 and upper and lower trays. A cross section of the recess is shown in FIG. 6.

Figure 6:
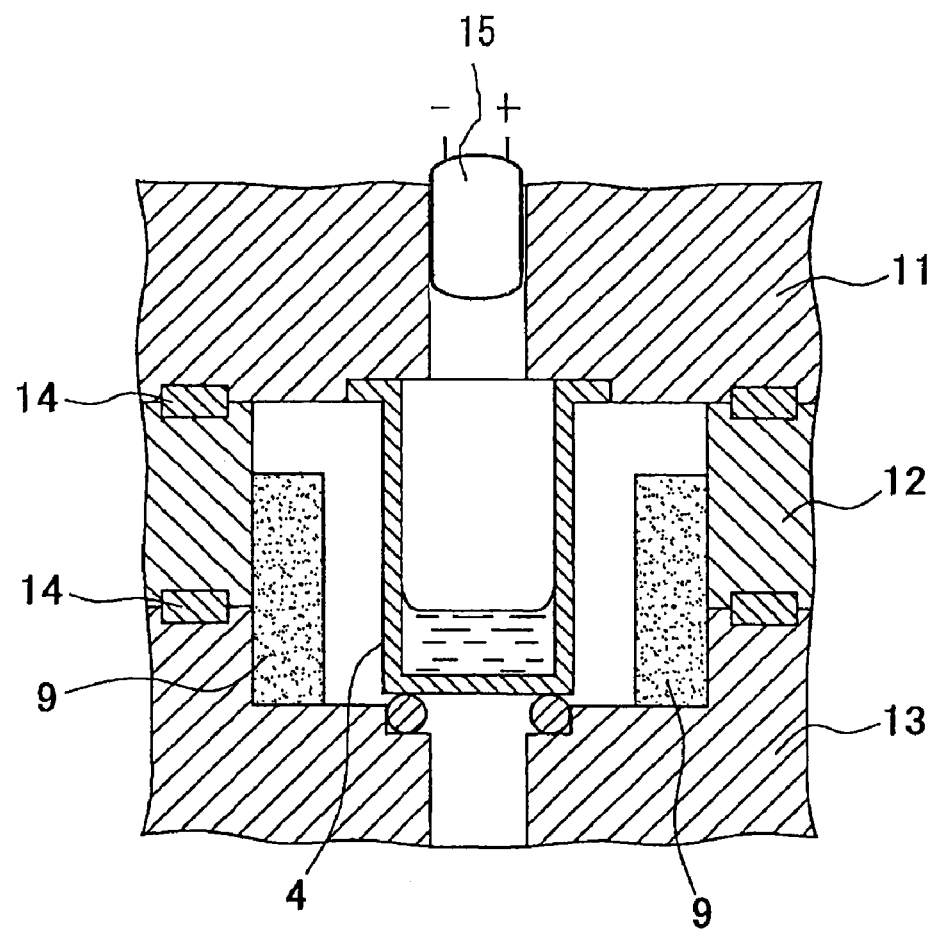
[FIG. 6] A cross section showing one state of accommodation attained by the incubation apparatus.

Referring to FIG. 6, the upper portion of a well unit 4 is in contact with a recessed portion formed in the bottom surface of the upper tray 11, whereas the lower portion of the well unit 4 is supported at the upper ends of holes 7 provided in the lower tray. Above the well unit 4, observation holes 5 are provided, and in each hole, an LED 15 of 620-mm wavelength is disposed so as to serve as a light source enabling observation. Below the well unit 4 are provided observation holes 7, which allow passage of light therethrough, enabling analysis of specimens contained in the wells through measurement of light intensity by use of a scanner. Also, porous material 9 is provided in the recess in order to hold liquid and to thereby maintain a saturated vapor pressure of the liquid contained in the wells. As described above, recesses are defined by the upper, middle, and lower trays and are separated from one another by their vicinity walls which serve as separators, wherein each recess has its own temperature-specific vapor pressure and is separated from another recess in terms of vapor pressure. With this configuration, in combination with the liquid contained in the porous material, liquid vapor generated on the high-temperature side is prevented from transferring to the low-temperature side, eliminating any chance of condensation.

The pipe defining a flow channel 2 is made of aluminum, and has an inner diameter of 8 mm. Referring to FIGS. 2 to 4 and FIG. 7, a set of 2 pipes is provided for each of the three trays and penetrating therethrough. This configuration is beneficial to achieve better heat conduction from the water at a constant temperature to the housing vessel. The two pipes are connected to each other outside the vessel by the mediation of a tube (not shown), and a fluid runs firstly in one direction then opposite direction along one side of the vessel, then enters a pipe provided for another tray that is connected to the previous tray, to thereby continue to pass through similar flow channels. The flow channel 3 also has the same configuration as the flow channel 2.

As described above, since the apparatus of Example 5 has recesses and long flow channels, incubation can be performed without incurring any local temperature non-uniformity. Moreover, observation holes facilitate observation and measurement of specimens, and also open the way to automation of analysis.

Example 6

Using an apparatus of Example 5, liquid culture of *E. coli* was performed, and growth curves were obtained for a temperature series of 43 to 50° C. The incubation apparatus was fixed on a scanner of an A4 size, and both the apparatus and the scanner were shaken at a frequency of 25 cycles/min, to thereby prevent sedimentation of the *E. coli* in each well. Since the light coming upward from the scanner is diffused excepting that from the center portion, a Fresnel lens was attached onto a moving photometric section, whereby the axes of light were corrected to become vertical to the horizontal plane.

Figure 8:
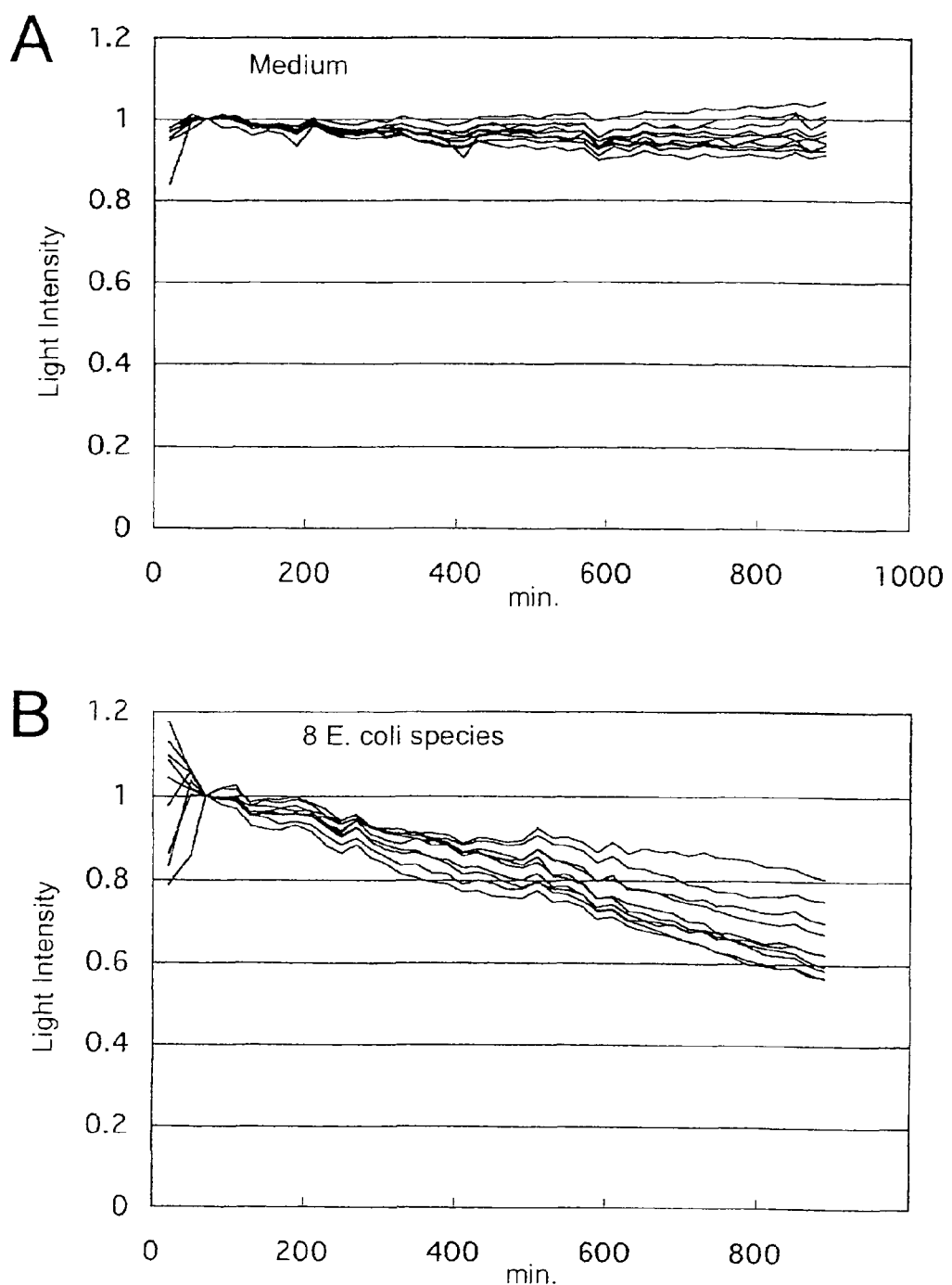
[FIG. 8] Growth curves obtained by use of the incubation apparatus.
Figure 9:
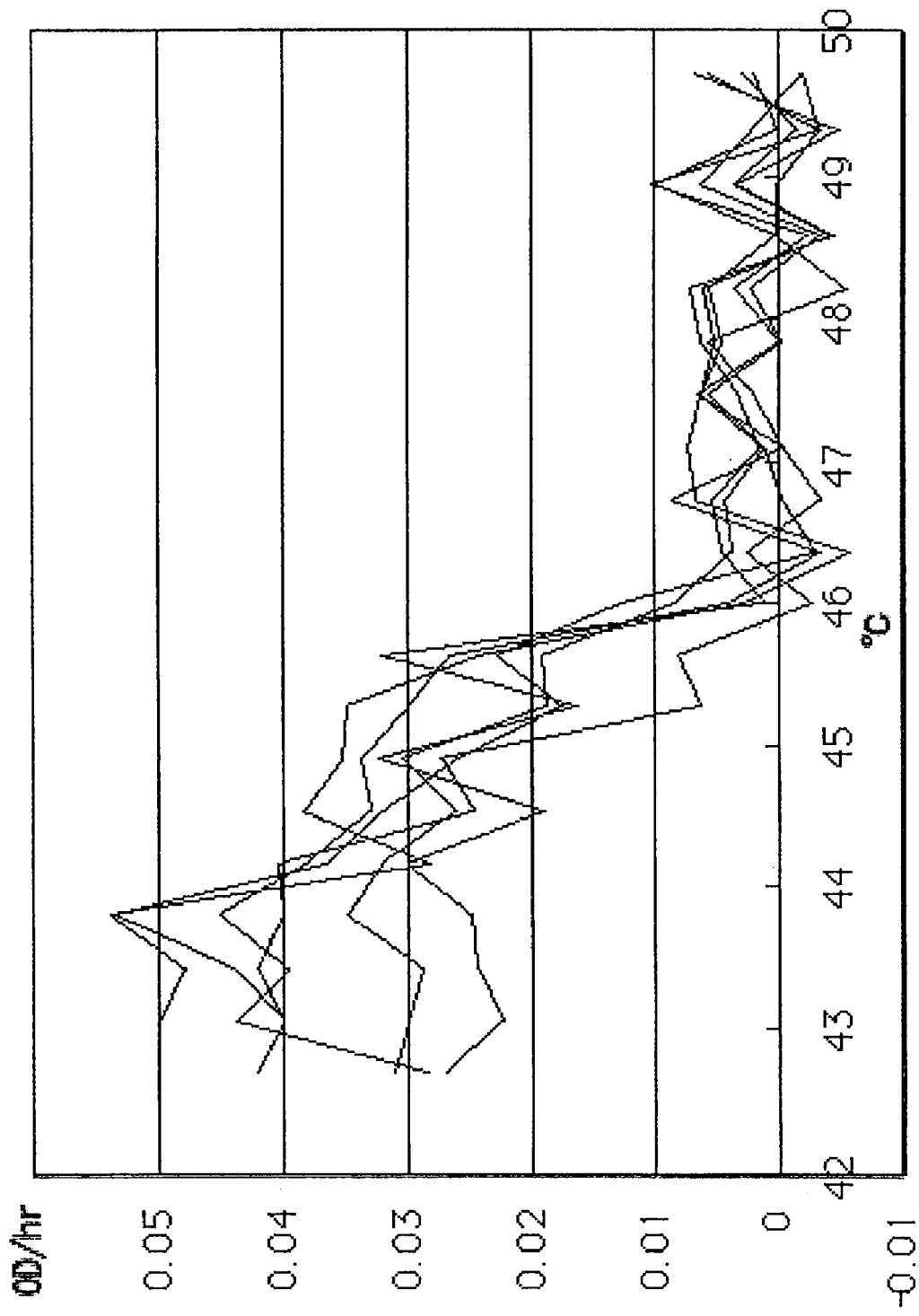
[FIG. 9] Growth rates obtained by use of the incubation apparatus.

Wells were filled with either an *E. coli* mutant or a wild type *E. coli* serving as a control, and also with a medium, but some wells were filled with the medium only with an aim to enable compensation of any difference in photometric efficiency which may be caused due to difference in conditions. Two 8-well units were placed at and assigned a certain fixed temperature. Since there are 20 rows of such a well unit combination, a total of 320 wells were analyzed simultaneously. Firstly, by using a scanner, a total of 321 measurements were obtained; i.e., for the 320 wells and the LED fitted in the center hole for correction purposes, whereby intensities of the light emitted from the 320 wells were corrected. Changes in light intensity were thus obtained over time, and were summarized in FIG. 8 as growth curves drawn on the basis of percent light transmission. The above experiment has revealed that measurement can be performed after 60 minutes in time, at which temperature stabilization was attained, that 6 cases in (A), representing time-course changes in light transmitted through medium, has reproducibility, and that growth curves for 8 *E. coli* strains in (B) at a certain temperature were confirmed to have reliability. The growth rates of the thus-measured 6 *E. coli* mutants at various temperatures are shown in FIG. 9.

INDUSTRIAL APPLICABILITY

The incubation apparatus of the present invention enables a user to perform incubation under different temperature conditions by use of a single apparatus. Also, with the present apparatus, analysis is easy and can be automated. Therefore, various economic effects, including labor saving, reduction in space for installing incubation devices, and reduction in operational cost, can be expected. Moreover, the apparatus eliminates the problem of moisture evaporated from specimens on the high-temperature side condenses to form dew on the low-temperature side. Therefore, the incubation apparatus of the present invention enables cultivation of microorganisms at different temperature conditions, which has heretofore been difficult; enables calculation of optimal culture temperatures; and also realizes proliferation of microorganisms whose temperature conditions are unknown.

The invention claimed is:

1. A multiwell incubation apparatus, comprising:
a well-housing vessel made of a heat conducting material;
wells to store liquid culture that are detachably housed in the well-housing vessel, the wells being arranged in transverse rows and longitudinal rows;
a liquid or gas flow channel or bath in the well-housing vessel that contains a liquid and that carries a first gas from one side of the flow channel or bath and a second gas from an opposite side of the flow channel or bath, to supply the first and second gases each saturated with vapor of the liquid, at varying mixing ratios between the wells of a transverse row along the flow channel or bath, the multiwell incubation apparatus maintaining incubation temperatures differing between individual transverse rows of the wells with a predetermined temperature difference, so that the temperatures realize a temperature series which forms a predetermined temperature difference profile along the longitudinal rows;
a heat source to realize a temperature which is a lowest in the temperature series, the heat source being disposed outside the well rows and along a closest transverse row to a first side of the well-housing vessel;
another heat source to realize a temperature which is a highest in the temperature series, said another heat source being disposed outside the well rows and along a side of the well-housing vessel opposite to the first side; and
a separator provided between each transverse row of a certain temperature.

2. The multiwell incubation apparatus according to claim 1, wherein two or more wells in each transverse row are combined to each other to form a well unit that is detachably housed in the well-housing vessel.

3. The multiwell incubation apparatus according to claim 1, further comprising:
a lid to cover all the wells.

4. The multiwell incubation apparatus according to claim 3, in which, when the lid is attached to the well-housing vessel, the lid has holes at positions above the wells, the well-housing vessel has holes at positions below the wells, and each of the holes in the lid and in the well-housing vessel has a diameter smaller than that of the wells.

5. The multiwell incubation apparatus according to claim 3, in which the well-housing vessel further includes a middle tray disposed under the lid.

6. The multiwell incubation apparatus according to claim 5, in which the well-housing vessel further includes a lower tray disposed under the middle tray,
the lid, the middle tray, and the lower tray each having cut-out portions that when aligned together, define recesses to contain the wells, and
the recesses including a porous material that holds liquid.

7. The multiwell incubation apparatus according to claim 3, further comprising:
a device to sterilize the lid and well-receiving portions of the well-housing vessel through irradiation with UV rays.

8. The multiwell incubation apparatus according to claim 3, in which, when the lid is attached to the well-housing vessel, the lid has well observation holes at positions above the wells or the well-housing vessel has well observation holes at positions below the wells, and each of the well observation holes in the lid or in the well-housing vessel has a diameter smaller than that of the wells and includes a mirror to reflect light to enable observation or a light source, allowing optical observation of substances contained in the wells.

9. The multiwell incubation apparatus according to claim 1, further comprising:
a shaker that moves the well-housing vessel.

10. The multiwell incubation apparatus according to claim 1, further comprising:
well separators disposed between the wells within a transverse row of a certain temperature, so that changes in oxygen partial pressure or in partial pressure of a specific gas between the wells within that transverse row are realized in a stepwise pattern.

11. An incubation method performed through use of the multiwell incubation apparatus as recited in claim 1, which method comprises:
adding specimens to the wells of the apparatus; and
achieving, by use of the heat source and along the first side of the well-housing vessel, the temperature which is the lowest within the predetermined temperature series, and also achieving, by use of said another heat source and along the side opposite to the first side, the temperature which is the highest within the predetermined temperature series, to thereby realize the incubation temperatures differing between the individual transverse rows of the wells, with the predetermined temperature difference.

12. The method of analysis according to claim 11, wherein the adding and achieving are partially or entirely automated.

13. A method of analysis of specimens, performed through use of the multiwell incubation apparatus as recited in claim 1, comprising:
irradiating specimens contained in the wells with light, and measuring light transmitted through the specimens or scattered light including fluorescence.

14. The method of analysis according to claim 13, further comprising:
at a time and by a movable device equipped with two or more photodetectors, measuring the transmitted light or the scattered light including florescence emitted from a single row of observation holes, and subsequently,
measuring light intensity in a scanning mode, in which rows are sequentially observed one by one in such a manner that the wells belonging to one row are observed at a time.

15. The method of analysis according to claim 13, which further comprises:
automatically forwarding obtained photometric data to a computer; and
automatically performing a numerical analysis suitable for growing cells or viruses, or allowing chemical reactions to proceed on the basis of multiwell incubation, to thereby automatically perform calculation of values of target parameters.

* * * * *